(12) United States Patent
Birnbaum et al.

(10) Patent No.: US 10,391,186 B2
(45) Date of Patent: *Aug. 27, 2019

(54) ACTINIUM-225 COMPOSITIONS OF MATTER AND METHODS OF THEIR USE

(71) Applicant: Los Alamos National Security, LLC, Los Alamos, NM (US)

(72) Inventors: Eva Rachel Birnbaum, Los Alamos, NM (US); Jonathan W. Engle, Los Alamos, NM (US); Francois Meiring Nortier, Los Alamos, NM (US)

(73) Assignee: Triad National Security, LLC, Los Alamos, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/420,058

(22) Filed: Jan. 30, 2017

(65) Prior Publication Data
US 2017/0202983 A1 Jul. 20, 2017

Related U.S. Application Data

(62) Division of application No. 14/507,094, filed on Oct. 6, 2014, now Pat. No. 9,555,140.

(60) Provisional application No. 61/887,510, filed on Oct. 7, 2013.

(51) Int. Cl.
*A61K 51/00* (2006.01)
*A61K 51/10* (2006.01)

(52) U.S. Cl.
CPC .......... *A61K 51/00* (2013.01); *A61K 51/1093* (2013.01)

(58) Field of Classification Search
CPC ..................................................... A61K 51/00
See application file for complete search history.

(56) References Cited

U.S. PATENT DOCUMENTS

| | | | |
|---|---|---|---|
| 6,187,037 B1 * | 2/2001 | Satz | A61K 51/12 600/3 |
| 7,736,610 B2 * | 6/2010 | Meikrantz | C22L 33/0005 423/249 |
| 2007/0243132 A1 * | 10/2007 | Russell-Jones | A61K 9/0014 424/1.11 |

OTHER PUBLICATIONS

Weidner et al., "Proton-Induced Cross Sections Relevant to Production of 225Ac and 223Ra in Natural Thorium Targets Below 200 MeV", Applied Radiation and Isotopes, Nov. 2012, 70, pp. 2602-2607.
Koch et al., "Production of AC-225 and Application of the Bi-213 Daughter in Cancer Therapy", Czechoslovak Journal of Physics, 1999, 49 (Suppl S1), pp. 817-822.
Zhuikov et al., "Production of 225Ac and 223Ra by Irradiation of Th with Accelerated Protons", Radiochemistry, 2011, 53(1), pp. 73-80.
Ermolaev et al., "Production of Actinium, Thorium and Radium Isotopes from Natural Thorium Irradiated with Protons up to 141 MeV", Radiochimica Acta, Apr. 2012, 100(4), pp. 223-229.

* cited by examiner

*Primary Examiner* — Michael G. Hartley
*Assistant Examiner* — Jagadishwar R Samala
(74) *Attorney, Agent, or Firm* — Lewis Roca Rothgerber Christie LLP

(57) ABSTRACT

The present invention is directed to improved methods for generating compositions comprising actinium-225.

2 Claims, 17 Drawing Sheets

ACTINIUM-225 COMPOSITIONS OF MATTER AND METHODS OF THEIR USE

CROSS REFERENCE TO RELATED APPLICATION

This application is a divisional of and claims priority to and the benefit of U.S. patent application Ser. No. 14/507,094, filed Oct. 6, 2014, now U.S. Pat. No. 9,555,140, which claims the benefit of U.S. Provisional Application No. 61/887,510, filed Oct. 7, 2013, the entire contents of which are incorporated by reference herein.

GOVERNMENT RIGHTS

The subject matter disclosed herein was made with government support under Contract No DE-AC52-06NA253 awarded by the National Nuclear Security Administration of the U.S. Department of Energy at Los Alamos National Laboratory. The subject matter disclosed herein was also made with government support by and award from the U.S. Department of Energy Office of Science, The Isotope Development and Production for Research and Applications subprogram in the Office of Nuclear Physics. The Government has certain rights in the herein disclosed subject matter.

BACKGROUND

Interest in alpha-emitting radioisotopes for therapeutic applications, especially the treatment of cancer using highly selective biological vectors, has grown steadily in recent years. Unfortunately, their development as anti-cancer agents has been hindered by the lack of a readily expandable supply chain. This is particularly true for Ac-225 ($t_{1/2}$=9.92 d, 100% α) and its daughter proposed for generator harvest, Bi-213 ($t_{1/2}$=45.6 min, 98% β-, 2% α), the availability of which has been predicated upon harvest from legacy stores of their shared, long-lived parent, Th-229. See FIGS. 1A-1C. The global feedstock of Th-229 is derived from molten thorium-salt breeder reactors, which produced fissile U-233 for reactor and weapons applications. With the growing need to secure quantities of special nuclear materials, future reactor production and dissemination of the U-233 parent of Ac-225 is extremely unlikely. Meanwhile, the current annual Ac-225 supply of approximately 1.7 Ci, which is distributed between United States, European, and Russian institutions, is unable to support large-scale clinical trials.

Modern theoretical comparisons of the cell-killing potential of various nuclides point encouragingly to Ac-225, whose daughters emit four highly energetic a-particles while decaying to stable Bi-209 and buttress policy directives at the national and international levels. Recent reports establish that proton irradiation of thorium targets are able to produce Curie-quantities of approximately 2 Ci (74 GBq) of Ac-225 in a single week's bombardment.

But concurrent with Ac-225 generation is the formation of undesirable radioisotopes. In particular, Ac-226 and Ac-227 are problematic because they follow the chemistry of Ac-225 in any chemical separation. Their removal requires mass separation techniques, which are cost prohibitive and have a throughput efficiency for Ac-225 that is likely to be <20%.

In addition, radioactive isotopes of lower lanthanide elements (lanthanum and cerium) limit the medical utility of the Ac-225 product of accelerator irradiations and removal of these isotopes from actinium is extremely challenging because of chemical similarities between actinium, lanthanum, and cerium.

As such, improved methods for the generation and purification of Ac-225 are needed.

SUMMARY

The present invention is directed to actinium-225 compositions comprising particular quotient of activity quantity ratios with actinium-226, actinium-227, cerium-139, cerium-141, cerium-143, and lanthanum-140. Devices incorporating these compositions are also described, as well as methods of using these compositions for the treatment of cancer.

DETAILED DESCRIPTION OF ILLUSTRATIVE EMBODIMENTS

Figure 1A:
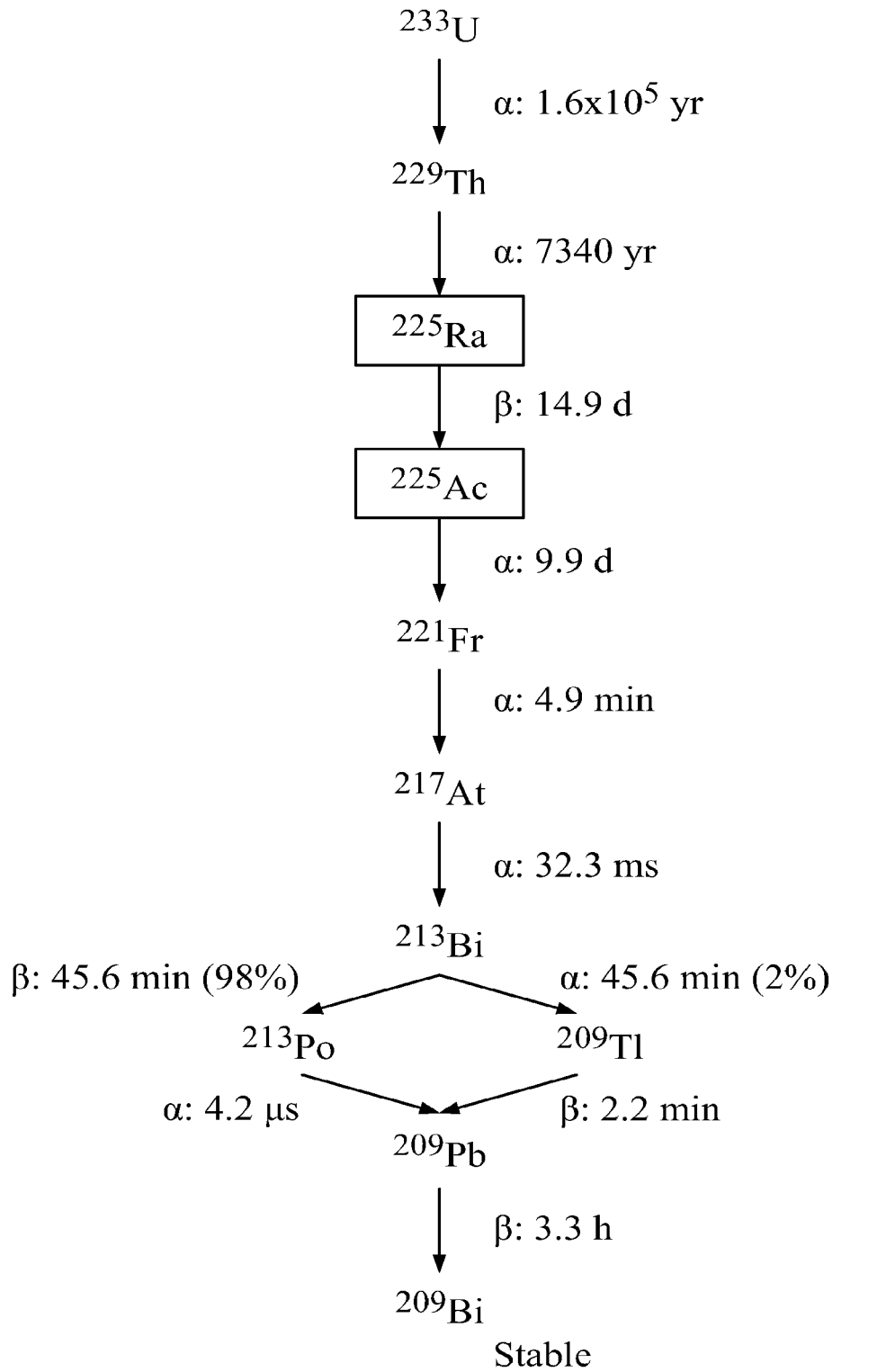
FIGS. 1A-1C depict decay schemes of U-233, U-234, and U-235, showing the decay chains of Ac-225, Ac-226, and Ac-227 indirectly. Isotopes with measured cross sections from Th(p,x)-232 reactions are identified by boxes.

All ranges disclosed herein are inclusive of the recited endpoint and independently combinable (for example, the range of "from 0.1 to 10" is inclusive of the endpoints, 0.1 and 10, and all the intermediate values).

The present invention is directed to methods of producing significant quantities of actinium-225. In addition to producing large quantities of this isotope, the methods of the invention also minimize the amount of undesirable isotopes, such as, for example, actinium-226, actinium-227, cerium-139, cerium-141, cerium-143, and lanthanum-140.

According to the invention, a thorium target, which is significantly thicker than those targets previously described, is irradiated with protons with an energy range between 180 and 80 MeV. This thick thorium target is irradiated for approximately 60,000,000 nano-Ampere-hours, which is a much longer time than previously described in the art. Weidner et al. (J. W. Weidner, S. G. Mashnik, K. D. John, F. Hemez, B. D. Ballard, H. Bach, E. R. Birnbaum, L. J. Bitteker, A. Couture, D. Dry, M. E. Fassbender, M. S. Guley, K. R. Jackman, J. L. Ullman, L. E. Wolfsberg, F. M. Nortier, Proton-induced cross sections relevant to production of $^{225}$Ac and $^{223}$Ra in natural thorium targets below 200 MeV, Applied Radiation and Isotopes, 70 (2012) 2602-2607) describes irradiating thin thorium foils (approximately 125 μm) that covered 12 discrete energies proton energies with 120 nano-Ampere-hours of proton beam. Weidner et al. measured the energy-dependent probability of resultant radioisotope formation, i.e., the cross sections. Those measured, discrete values were used to hypothesize a calculated yield of Ac-225 and 3 other radioisotopes integrating over two arbitrary energy ranges commensurate with the capabilities of the Los Alamos Isotope Production Facility and the Brookhaven Linac Isotope Producer (from 93 to 72 MeV and from 195 to 183 MeV respectively).

The capacity for deposited beam power in the methods of the invention exceeds that of the foils or previous calculations by factors of 10 to 1000. This improvement requires a substantially "thicker" target along the axis of the proton beam's direction of travel, enabling the formation of much larger quantities of Ac-225. As such, targets for use in the invention will be approximately 3 mm thick. This is in contrast to targets used previously, which were only about 125 μm thick. This improvement also improves the ratio of Ac-225 to other radioisotopic impurities such as Ac, Ce, and La.

"Thick targets" for use in the invention are much larger than those previously described in the art. Targets for use in the invention will be large enough in cross-sectional area to be exposed to a production-scale beam current, which is typically a disc approximately 5 cm in diameter. The use of larger targets in the methods of the invention will produce target masses of a few tens of grams. This larger target mass has significant effects on downstream chemistries for the purification of Ac-225.

According to the invention, a target containing thorium is introduced to a beam of accelerated particles to initiate a variety of nuclear reactions. These nuclear reactions form Ac-225, as well as Ac-226, Ac-227, Ce-139, Ce-141, Ce-143, La-140, and Ba-140 by "direct" and "indirect" mechanisms, e.g., producing the product nuclide directly via a single reaction or by requiring the decay of parent isotopes to form the daughter nuclide indirectly. The incident energy of the accelerated particle beam must be above 70 MeV, and ideally between 70 and 200 MeV, and, after passing through the target material, must retain an energy of above 50 MeV, and ideally between 50 and 190 MeV. These parameters will yield high quantities of Ac-225 as compared to the undesired, co-produced isotopes Ac-226, Ac-227, Ce-139, Ce-141, Ce-143, La-140. For example, using the methods of the invention, compositions comprising the following quotient of activity ratios are obtained:

actinium-226/actinium-225 less than 10;
actinium-227/actinium-225 less than 0.01;
cerium-139/actinium-225 less than 0.1;
cerium-141/actinium-225 less than 5;
cerium-143/actinium-225 less than 10; and
lanthanum-140/actinium-225 less than 5.

Preferably, these activity ratios are measured at the "end of bombardment." Those skilled in the art readily understand the scope of the term "end of bombardment."

In other embodiments, the following quotient of activity ratios are obtained:

actinium-226/actinium-225 less than 25;
actinium-227/actinium-225 less than 0.02;
cerium-139/actinium-225 less than 0.1;
cerium-141/actinium-225 less than 20;
cerium-143/actinium-225 less than 70; and
lanthanum-140/actinium-225 less than 20.

Preferably, these activity ratios are measured at the "end of bombardment."

In other embodiments, compositions comprising the following quotient of activity ratios are obtained:

actinium-226/actinium-225 between 0.1 and 10;
actinium-227/actinium-225 between 0.0001 and 0.01;
cerium-139/actinium-225 between 0.005 and 0.1;
cerium-141/actinium-225 between 0.1 and 5;
cerium-143/actinium-225 0.5 and 10; and
lanthanum-140/actinium-225 between 0.1 and 5.

Preferably, these activity ratios are measured at the end of bombardment.

In other embodiments, the following quotient of activity ratios are observed:

actinium-226/actinium-225 between 0.2 and 25;
actinium-227/actinium-225 between 0.0001 and 0.02;
cerium-139/actinium-225 between 0.001 and 0.1;
cerium-141/actinium-225 between 0.03 and 20;
cerium-143/actinium-225 0.1 and 70; and
lanthanum-140/actinium-225 between 0.03 and 20.

Preferably, these activity ratios are measured at the end of bombardment.

Methods of the invention can also produce compositions comprising the following quotient of activity ratios:

actinium-226/actinium-225 less than 8;
actinium-227/actinium-225 less than 0.01;
cerium-139/actinium-225 less than 0.05;
cerium-141/actinium-225 less than 5;
cerium-143/actinium-225 less than 8; and
lanthanum-140/actinium-225 less than 2.

Preferably, these activity ratios are measured at the end of bombardment.

In other embodiments, compositions of the disclosure comprise the following quotient of activity ratios:

actinium-226/actinium-225 less than 8;
actinium-227/actinium-225 less than 0.01;
cerium-139/actinium-225 less than 0.05;

cerium-141/actinium-225 less than 6;
cerium-143/actinium-225 less than 20; and
lanthanum-140/actinium-225 less than 6.

Preferably, these activity ratios are measured at the end of bombardment.

In other embodiments, compositions comprising the following quotient of activity ratios are obtained:
actinium-226/actinium-225 between 4 and 8;
actinium-227/actinium-225 between 0.001 and 0.01;
cerium-139/actinium-225 between 0.01 and 0.05;
cerium-141/actinium-225 between 0.1 and 5;
cerium-143/actinium-225 2 and 8; and
lanthanum-140/actinium-225 between 0.5 and 2.

In other embodiments, compositions comprise the following quotient of activity ratios:
actinium-226/actinium-225 between 0.6 and 8;
actinium-227/actinium-225 between 0.0005 and 0.01;
cerium-139/actinium-225 between 0.005 and 0.05;
cerium-141/actinium-225 between 0.1 and 6;
cerium-143/actinium-225 0.3 and 20; and
lanthanum-140/actinium-225 between 0.1 and 6.

Preferably, these activity ratios are measured at the end of bombardment.

Ratios of isotopes are determined by the amount of production of each isotope in the thick target over the course of irradiation. These ratios can be predicted using the cross sections that have been measured across the relevant energy range. Production rates must be effectively integrated over the relevant energy range, which will depend on the incident energy onto the target, target density, and target thickness, since protons lose energy through atomic interactions as they move through the target. Isotopes are decaying during production, so the final isotope ratios will also depend on total irradiation time and isotopes' characteristic decay times. All of these parameters must be considered to determine isotope ratios in a useful target, e.g., one that is irradiated for sufficient time and is of sufficient thickness to produce a useful quantity of the desired isotope, Ac-225.

In addition to producing the desired Ac-225 isotope, irradiation also produces undesired isotopes, which limit the clinical utility of the final Ac-225 product. The methods of the invention, however, produce compositions having higher quantities of Ac-225, as compared to other radioisotopes such as Ce-139, Ce-141, Ce-143, and La-140. Moreover, the decay of these undesired radioisotopes over time, for example, 1, 3, 5, 7, 10, 15, 20, 25, or 30 days after the end of bombardment, provides additional methods to maximize the isotopic purity of Ac-225.

A number of chemical separation procedures for actinide separations exist. Applying these protocols to an irradiated thorium target to isolate Ac-225 will result in the isolation of Ac-225 with unique isotope ratios over time, for example, 1, 3, 5, 7, 10, 15, 20, 25, or 30 days after the end of bombardment. Material ratios after separation are determined from the isotope ratios at the end of bombardment, the efficacy of the chosen chemical purification process, and then accounting for decay that occurs for each isotope during the time required to conduct separation. Chemical separation will further improve cerium and lanthanum ratios.

Methods of the invention can also produce compositions, after purification and following the end of bombardment, comprising the following quotient of activity ratios:
actinium-226/actinium-225 less than 10;
actinium-227/actinium-225 less than 0.01;
cerium-139/actinium-225 less than 0.008;
cerium-141/actinium-225 less than 0.1;
cerium-143/actinium-225 less than 0.01; and
lanthanum-140/actinium-225 less than 0.01.

Preferably, these activity ratios are measured at between 1 and 30 days after the end of bombardment, for example, measured at 1, 3, 5, 7, 10, 15, 20, 25, or 30 days after the end of bombardment.

In other embodiments, compositions, after purification and following the end of bombardment, comprise the following quotient of activity ratios:
actinium-226/actinium-225 less than 1;
actinium-227/actinium-225 less than 0.03;
cerium-139/actinium-225 less than 0.3;
cerium-141/actinium-225 less than 30;
cerium-143/actinium-225 less than 1; and
lanthanum-140/actinium-225 less than 1.

Preferably, these activity ratios are measured at between 1 and 30 days after the end of bombardment, for example, measured at 1, 3, 5, 7, 10, 15, 20, 25, or 30 days after the end of bombardment.

In other embodiments, compositions comprising the following quotient of activity ratios are obtained:
actinium-226/actinium-225 between 0.001 and 10;
actinium-227/actinium-225 between 0.0005 and 0.01;
cerium-139/actinium-225 between $1 \times 10^{-5}$ and 0.008;
cerium-141/actinium-225 between $1 \times 10^{-5}$ and 0.1;
cerium-143/actinium-225 between $1 \times 10^{-6}$ and 0.01; and
lanthanum-140/actinium-225 between $1 \times 10^{-6}$ and 0.01.

Preferably, these activity ratios are measured at between 1 and 30 days after the end of bombardment, for example, measured at 1, 3, 5, 7, 10, 15, 20, 25, or 30 days after the end of bombardment.

In other embodiments, compositions comprising the following quotient of activity ratios are obtained:
actinium-226/actinium-225 less than 0.05;
actinium-227/actinium-225 less than 0.01;
cerium-139/actinium-225 less than 0.01;
cerium-141/actinium-225 less than 10;
cerium-143/actinium-225 less than 0.3; and
lanthanum-140/actinium-225 less than 0.3.

Preferably, these activity ratios are measured at between 1 and 30 days after the end of bombardment, for example, measured at 1, 3, 5, 7, 10, 15, 20, 25, or 30 days after the end of bombardment.

Methods of the invention can also produce compositions, after purification and following the end of bombardment, comprising the following quotient of activity ratios:
actinium-226/actinium-225 less than 3;
actinium-227/actinium-225 less than 0.01;
cerium-139/actinium-225 less than 0.01;
cerium-141/actinium-225 less than 0.01;
cerium-143/actinium-225 less than 0.001; and
lanthanum-140/actinium-225 less than 0.001.

Preferably, these activity ratios are measured at between 1 and 30 days after the end of bombardment, for example, measured at 1, 3, 5, 7, 10, 15, 20, 25, or 30 days after the end of bombardment.

Methods of the invention can also produce compositions, after purification and following the end of bombardment, comprising the following quotient of activity ratios:
actinium-226/actinium-225 between 0.001 and 1; and
actinium-227/actinium-225 0.00003 and 0.03.

Preferably, these activity ratios are measured at between 1 and 30 days after the end of bombardment, for example, measured at 1, 3, 5, 7, 10, 15, 20, 25, or 30 days after the end of bombardment.

In other embodiments, compositions comprising the following quotient of activity ratios are obtained:

actinium-226/actinium-225 between 0.001 and 3;
actinium-227/actinium-225 between 0.001 and 0.01;
cerium-139/actinium-225 between $1\times10^{-5}$ and 0.01;
cerium-141/actinium-225 between $1\times10^{-5}$ and 0.01;
cerium-143/actinium-225 between $1\times10^{-6}$ and 0.001; and
lanthanum-140/actinium-225 between $1\times10^{-6}$ and 0.001.

Preferably, these activity ratios are measured at between 1 and 30 days after the end of bombardment, for example, measured at 1, 3, 5, 7, 10, 15, 20, 25, or 30 days after the end of bombardment.

In other embodiments, compositions comprising the following quotient of activity ratios are obtained:
actinium-226/actinium-225 between 0.005 and 0.05; and
actinium-227/actinium-225 between 0.001 and 0.01.

Preferably, these activity ratios are measured at between 1 and 30 days after the end of bombardment, for example, measured at 1, 3, 5, 7, 10, 15, 20, 25, or 30 days after the end of bombardment.

Example radioisotopic compositions at the end of a 10-day, 250-μA proton irradiation of a 10-gram thorium target with an incident energy of 93 MeV are shown in Table I below. For this example case, ratios of the actinium radioisotopes can only be affected by radioactive decay during the stated 10-day period, and so remain relatively (but predictably) altered as a function of time following chemical isolation procedures. Ratios of La-140 and, to lesser extent because of improved separations technology, Ce-139, -140, and -143, are altered both by decay and by achievable separation factors from actinium which range up to $10^3$.

TABLE 1

Example radioisotopic compositions at end of bombardment

| Isotope | (GBq) | (Ci) | Ratio to $^{225}$Ac |
|---|---|---|---|
| $^{225}$Ac | 52 | 1.4 | unity |
| $^{226}$Ac | 66 | 1.8 | 1.2 |
| $^{227}$Ac | 0.1 | 3E-3 | 0.002 |
| $^{139}$Ce | 0.7 | 0.02 | 0.014 |
| $^{141}$Ce | 103 | 2.8 | 2.0 |
| $^{143}$Ce | 347 | 9.4 | 6.714 |
| $^{140}$La | 46 | 1.3 | 0.929 |

In addition to direct therapeutic applications of Ac-225, the invention allows for Ac-225 to be immobilized in a device such as a medical generator such that the daughter isotopes, in particular Bi-213, can be selectively removed. For example, Bi-213 can be selectively removed with multiple elutions from the device and used for therapeutic applications. Generally, sufficient quantities of Bi-213 will be obtained within 30 days. Preferably, sufficient quantities of Bi-213 will be generated within 1, 3, 5, 7, 10, 12, 15, 18, 20, 25, or 30 days.

The compositions of the invention are useful for treating cancer. For example, the compositions of the invention can be used to treat breast cancer, a leukemia, a lymphoma, brain cancer, liver cancer, lung cancer, melanoma, ovarian cancer, prostate cancer, pancreatic cancer, or bone cancer.

EXAMPLES

Materials and Methods
Irradiation

Briefly, in two separate irradiations at the Los Alamos National Laboratory's Neutron Science Center (LANSCE), proton beams of approximately 90-120 nA intensities with incident energies of 100 and 200 MeV were impinged upon two thorium foil "stacks". Each stack contained two sets of six thin thorium foils separated by aluminum energy degraders. The $^{27}$Al(p,x)$^{22}$Na nuclear reaction was used to monitor proton flux, and Gafchromic film was exposed to irradiated stainless steel foils to monitor beam location and profile in the plane perpendicular to that of the foils. From each stack, one set of thorium foils was employed for α-counting following dissolution and chemical separation to isolate Ac-227, and the other set of foils was assayed by nondestructive γ-counting for a period of 10 months following the end of bombardment.

Alpha Spectroscopy of Ac-227

Cross sections for Ac-227 presented here are the result of measurements of Ac-227's short-lived daughter, Po-215 (t½=1.781 ms, 100% α, 2.3E-4% β-), by α-spectroscopy of separated solutions. The weak β-emissions of Ac-227 make the isotope's direct detection in mixed solutions difficult. For this reason, chemical separation has been performed to isolate 227Ac's signal from other radioisotopes present in solution. B. L. Zhuikov, S. N. Kalmykov, S. V. Ermolaev, R. A. Aliev, V. M. Kokhanyuk, V. L. Matushko, I. G. Taranaev, B. F. Myasoedov, Production of Ac-225 and Ra-223 by irradiation of Th with accelerated protons, Radiokhimiya, 53 (2011) 73-80. The cross section for production of Ac-227 by Th-232(p,2p4n) and Th-232(p,α2n) has recently been extended to approximately 160 MeV with measurements conducted at the Russian Institute for Nuclear Research. S. V. Ermolaev, B. L. Zhuikov, V. M. Kokhanyuk, V. L. Matushko, S. N. Kalmykov, R. A. Aliev, I. G. Taranaev, B. F. Myasoedov, Production of actinium, thorium and radium isotopes from natural thorium targets irradiated with protons up to 141 MeV, Radiochimica Acta, 100 (2012) 223-229. This work extends the measured cross section to 200 MeV.

Figure 2:
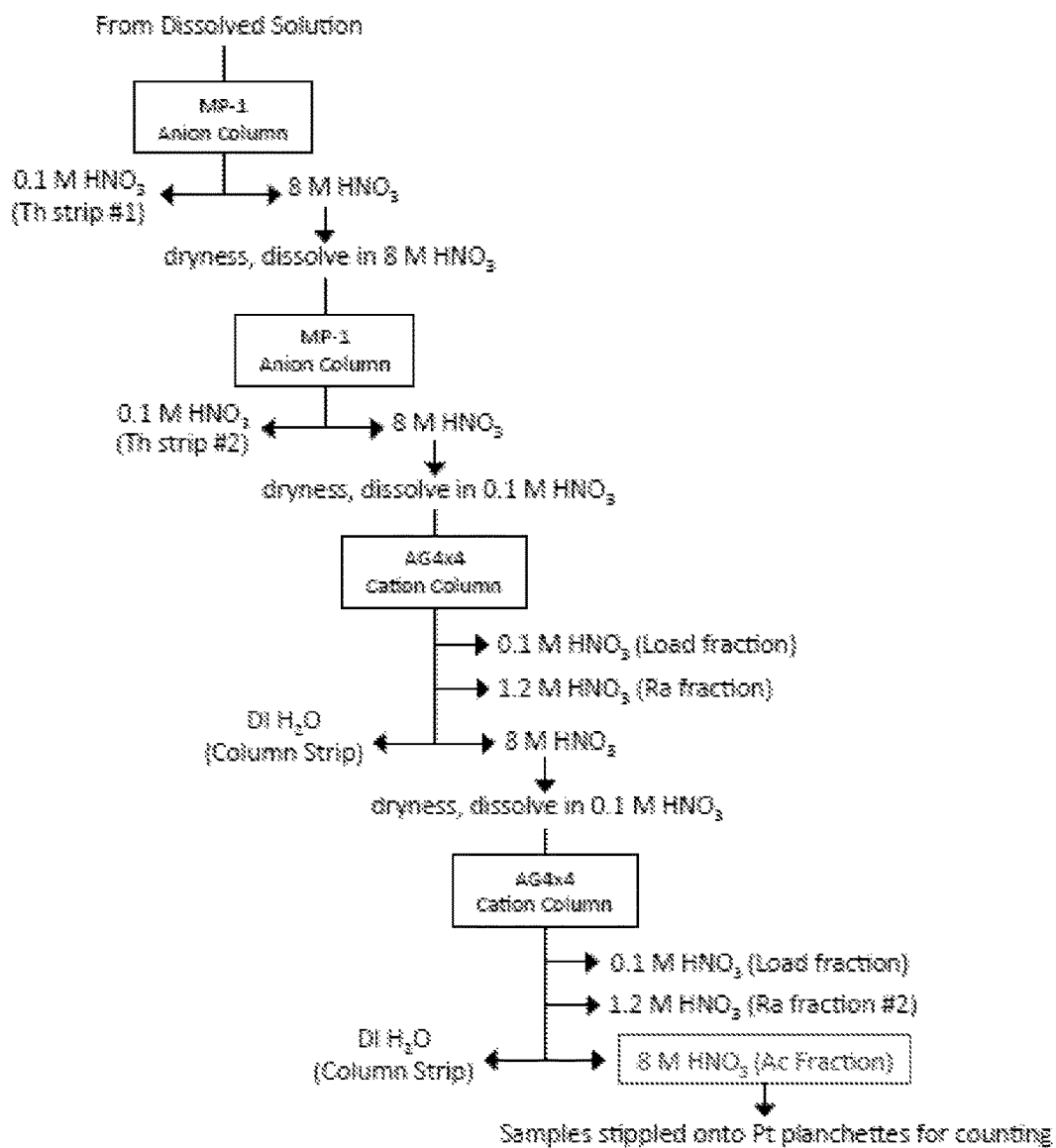
FIG. 2 depicts a chemical separation scheme for Ac-227.

A chemical process developed at Oak Ridge National Laboratory for routine separation of actinium and radium from a thorium matrix was used to isolate Ac-227 for counting with a few minor alterations (FIG. 2). R. A. Boll, D. Malkemus, S. Mirzadeh, Production of actinium-225 for alpha particle mediated radioimmunotherapy, Applied Radiation Isotopes, 62 (2005) 667-679. Thorium foils were dissolved using optima grade 15M HNO$_3$ (40 mL) and 1M HF (4 mL) stirred in solution overnight. The following day the thorium solution was taken to dryness using heat. The thorium solution matrix was changed using 3×50 mL of 8M HNO$_3$ washes, each taken to dryness before the next was added. The residue from the matrix conversion steps was then dissolved in 2 mL 8M HNO$_3$ and loaded onto a 10 mL bed volume BioRad MP1 anion exchange column. After loading the thorium, the column was washed with 30 mL 8M HNO$_3$. All fractions were collected for analysis. Thorium was stripped from the column by washing with 4×5 mL 0.1M HNO$_3$. Following separation of actinium and radium from the bulk thorium matrix, a second 5 mL bed volume anion column was run following the above procedure. The actinium/radium fraction was taken to dryness and the matrix was converted to 0.1M HNO$_3$ by 3×10 mL washes of 0.1M HNO$_3$. Again, each wash was taken to dryness before the next was added. Actinium was next isolated from radium with BioRad AG 50WX4 cation resin (10 mL bed volume equilibrated with 0.1M HNO$_3$). The radium/actinium residue was redissolved in 2 mL 0.1M HNO$_3$ and loaded onto the column. The column was then washed with 4×5 mL 0.1M HNO$_3$, which was collected as the load fraction. Radium was then stripped from the column by washing with 4×5 mL 1.2M HNO$_3$, and actinium was eluted with 4×5 mL 8M HNO$_3$. To ensure the complete separation of radium and actinium the above process was repeated using the collected actinium fraction as the initial radium/actinium fraction. The above procedure was repeated for each individual foil. The recovered actinium fractions were then taken to dryness and redissolved in 1 mL of 0.1M $HNO_3$ of which 50 µL was stippled onto a ¾" diameter platinum planchette with a spot diameter of approximately 1 cm and dried by gentle heating. The dried, stippled samples were then flame dried and assayed.

In order to determine the yield of actinium from the separation scheme outlined in FIG. 2 an unirradiated thorium foil was dissolved as described above and spiked with 5 µCi of Ac-225 concurrently, a second 5 µCi sample of Ac-225 was placed in 20 mL of 0.1 M $HNO_3$ and subsequently divided into 4 counting standards. The dissolved solution was split into 4 individual samples and each sample was separated using the described method above. Following separation the actinium fraction was taken to dryness, redissolved in 5 mL of 0.1 M $HNO_3$, and sat overnight to allow Fr-221 and Bi-213 daughter nuclei to reach equilibrium with the parent Ac-225. Following the separation the samples were counted on an HPGe detector (1 min count length), and the integrated counts were compared with those obtained from the 5 mL standards counted in the same geometry. Table 2 gives recovery yields for the Ac-225.

Measured Data

Cross section values measured in embodiments of the present invention are plotted in FIGS. 6-12 and collected in Table 3.

When compared with measurements reported here, the predictive power of the CEM03.03 event generator is qualitatively superior to ABLA+INCL and Bertini. All models are discrepant from measured data for Ac-226 and Ac-227 by approximately a factor of two between approximately 80 and 140 MeV. For Ce-139, the predictions of the Bertini event generator exceed measured values by more than a factor of four across much of the energy range below 200 MeV, while CEM03.03 and INCL+ABLA under-predict the measured data by only a factor of approximately 1.5. In general, all codes' agreement with measured data improves significantly for Ce-141, Ce-143, La-140 and Ba-140. This is especially true for CEM03.03 and Bertini, which show satisfactory agreement with measured data for the same four radioisotopes, while ABLA+INCL consistently returns values between two and three times higher than those produced from experiment. These cerium and lanthanum fission products will be important to the final radioisotopic purity of Ac-225 produced from thorium targets thanks to cumulative cross sections in the tens of millibarns, since, as noted above, Ba-140 decays with a 12.75 day half life to La-140.

TABLE 2*

| Ac-Standard | | | Following Separation | | | $^{225}$Ac Recovery | | |
|---|---|---|---|---|---|---|---|---|
| | Counts in Peak | | | Counts in Peak | | | Percentage | |
| Sample No. | 218 keV | 440 keV | Sample No. | 218 keV | 440 keV | Sample No. | 218 keV | 440 keV |
| 1 | 2042 | 2168 | 1 | 1817 | 1933 | 1 | 89.0% | 89.2% |
| 2 | 2054 | 2172 | 2 | 1827 | 1924 | 2 | 88.9% | 88.6% |
| 3 | 2034 | 2163 | 3 | 1815 | 1933 | 3 | 89.2% | 89.4% |
| 4 | 2039 | 2160 | 4 | 1818 | 1925 | 4 | 89.2% | 89.1% |
| Average | 2042.3 | 2165.8 | Average | 1819.25 | 1928.75 | Average | 89.1% | 89.1% |
| ±(SD) | 8.5 | 5.3 | ±(SD) | 5.3 | 4.9 | ±(SD) | 0.1% | 0.3% |

*Count values are integrated counts in the ROI

Figure 3:
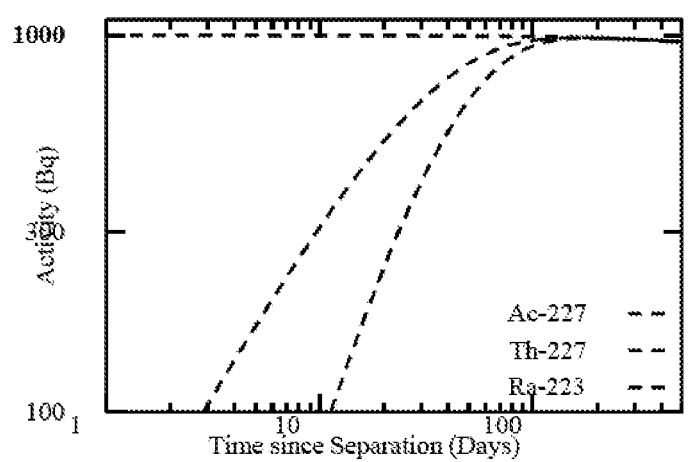
FIG. 3 depicts a Log-log plot of Ac-227, Th-227, and Ra-223 decay and in-growth as a function of time, showing the requisite waiting period necessary to allow the shorter-lived daughters Rn-219 and, finally Po-215 to reach equilibrium. Original activity of Ac-227 is arbitrarily normalized to 1 kBq. On the time-scale of the figure, the activity curves of Rn-219 and Po-215 are indistinguishable from the curve of Ra-223.

Because the α-branch of Ac-227 is weak and lower in energy (4.95 MeV) than the α-emissions of its daughter nuclides, the most easily observable signal to use for quantification of cleanly separated Ac-227 was that of Po-215's α-particle (7.39 MeV, Iα=99.9998%). It was necessary to allow the daughters of Ac-227 preceding Po-215, namely Th-227, Ra-223, and Rn-219, to reach equilibrium with their parent to facilitate this spectroscopic measurement. This required an approximately 100-day waiting period following chemical separation (see FIG. 3).

Figure 4:
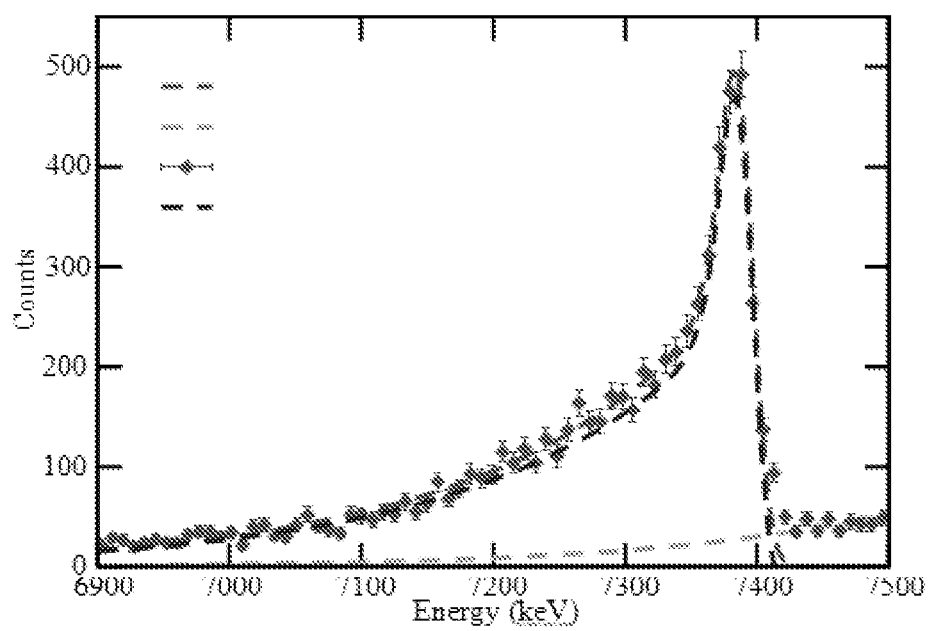
FIG. 4 depicts an alpha spectrum taken from the separated solution of a thorium foil irradiated at 160 MeV, showing raw data of the 7.39 MeV Po-215 peak used to quantify Ac-227 (red points), its fitted two-tailed Bortels function (red line), the fitted and subtracted tailing from the 7.69 MeV peak of Po-214 (green), and the final curve used for integration of peak area (blue).
Figure 5:
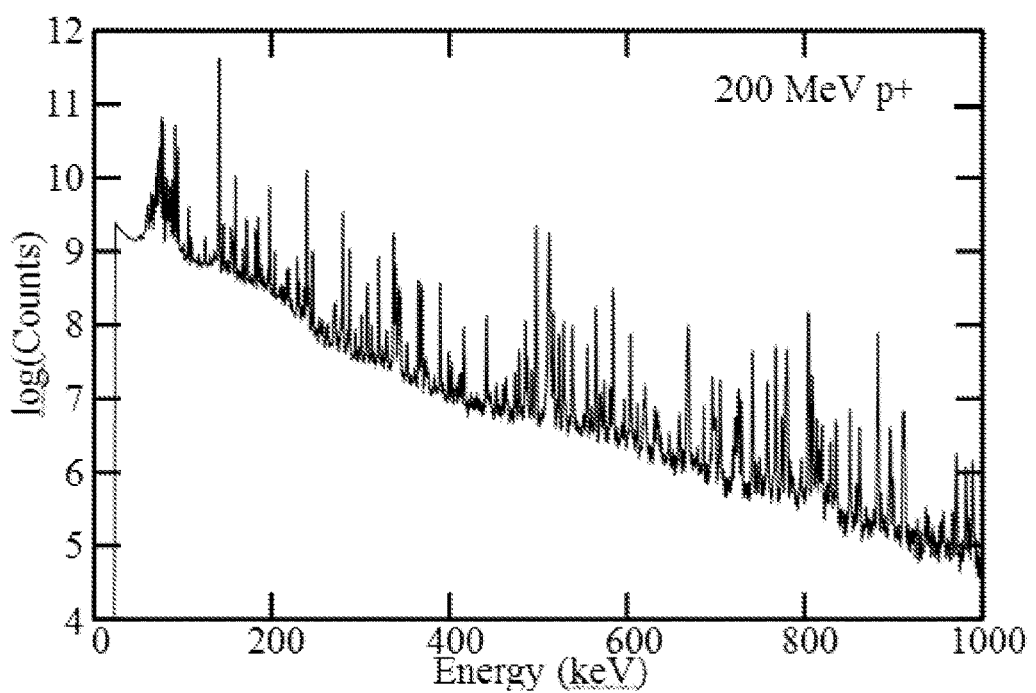
FIG. 5 depicts an example gamma spectrum collected from thorium foil irradiated at 200 MeV, 20 days following the end of irradiation.

Raw alpha spectra were analyzed by fitting the Po-215 peak of interest and any discernable peaks higher in energy than this peak with a two-tailed Bortels' function [17]. Counts were corrected for geometric efficiency, and measured background and tailing from the higher energy peak(s) were subtracted (FIG. 4). Final values were decay corrected and used to calculate Ac-227 cross sections using the well-known activation formula. Measured backgrounds in any channel used for integration of the Po-215 α-peak did not exceed 1% of the total true counts in that channel.

Agreement between values measured by embodiments of the present invention and previous experimental measurement is generally good. Values measured by Holub and Yaffe [R. Holub, L. Yaffe, Charge dispersion studies of heavy-mass elements in the fission of Th-232 by protons of medium energy, Journal of Inorganic and Nuclear Chemistry, 35 (1973)] for lanthanide radioisotopes are uniformly lower by less than a factor of two than those reported by Titarenko and coauthors [Y. E. Titarenko, V. F. Batyaev, E. I. Karpikhin, R. D. Mulambetov, A. B. Koldobsky, V. M. Zhivun, S. V. Mulambetova, K. A. Lipatov, Y. A. Nekrasov, A. V. Belkin, N. N. Alexeev, V. A. Schegolev, Y. M. Goryachev, V. E. Luk'yashin, E. N. Firsov, Experimental and Theoretical Study of the Yields of Residual Product Nuclei Produced in Thin Targets Irradiated by 100-2600 MeV Protons, in: Y. E. Titarenko (Ed.), International Nuclear Data Committee of the International Atomic Energy Agency, Vienna, Austria, 2003] and by embodiments of the present invention.

TABLE 3

Cross sections measured in the invention and the predictions of MCNP6 event generators CEM03.03, Bertini, and ABLA + INCL

| Energy (MeV) | ΔE (MeV) | σ (mb) | Δσ (mb) | E (MeV) | CEM03.03 (mb) | Bertini (mb) | INCL + RAL (mb) |
|---|---|---|---|---|---|---|---|
| Ac-227 Invention | | | | | | | |
| 194.5 | 0.3 | 13.9 | 1.8 | 200 | 29.3 | 16.6 | 25.5 |
| 178.3 | 0.7 | 14.2 | 1.8 | 190 | 28.8 | 17.2 | 25.6 |
| 160.7 | 1.0 | 15.5 | 1.9 | 180 | 29.5 | 17.4 | 26.2 |
| 141.8 | 1.3 | 14.2 | 1.8 | 170 | 29.3 | 18.1 | 26.7 |
| 120.9 | 1.6 | 10.9 | 1.4 | 160 | 29.4 | 18.7 | 26.8 |
| 97.0 | 2.0 | 8.8 | 1.1 | 150 | 30.2 | 20.0 | 27.2 |
| 90.8 | 0.4 | 6.6 | 0.8 | 140 | 28.0 | 20.9 | 27.4 |
| 81.7 | 0.6 | 5.6 | 0.7 | 130 | 26.1 | 21.9 | 26.9 |
| 72.8 | 0.7 | 2.8 | 0.3 | 120 | 25.1 | 22.9 | 26.6 |
| 64.9 | 0.9 | 2.6 | 0.3 | 110 | 22.6 | 23.4 | 26.2 |
| 56.3 | 1.1 | 2.1 | 0.2 | 100 | 13.5 | 23.0 | 23.1 |
| 44.0 | 1.4 | 4.0 | 0.5 | 90 | 10.0 | 19.9 | 20.2 |
| | | | | 80 | 5.5 | 15.0 | 15.2 |
| | | | | 70 | 1.2 | 8.8 | 9.0 |
| | | | | 60 | 0.0 | 4.2 | 2.6 |
| | | | | 50 | 0.0 | 3.1 | 0.1 |
| | | | | 40 | 0.0 | 6.9 | 0.0 |
| Ac-226 Invention | | | | | | | |
| 194.5 | 0.3 | 15.7 | 1.1 | 200 | 13.6 | 21.6 | 25.1 |
| 178.3 | 0.7 | 17.2 | 1.3 | 190 | 14.1 | 22.4 | 24.5 |
| 160.7 | 1.0 | 16.0 | 1.1 | 180 | 15.1 | 23.3 | 25.0 |
| 141.8 | 1.3 | 14.2 | 1.3 | 170 | 15.7 | 23.0 | 24.9 |
| 120.9 | 1.6 | 12.8 | 0.8 | 160 | 16.5 | 23.3 | 24.6 |
| 97.0 | 2.0 | 8.4 | 0.5 | 150 | 17.9 | 23.0 | 24.0 |
| 90.8 | 0.4 | 7.5 | 0.4 | 140 | 19.4 | 23.4 | 23.1 |
| 81.7 | 0.6 | 4.9 | 1.4 | 130 | 20.8 | 23.2 | 21.9 |
| 72.8 | 0.7 | 4.3 | 0.2 | 120 | 21.5 | 22.4 | 20.1 |
| 64.9 | 0.9 | 4.9 | 0.2 | 110 | 21.3 | 20.6 | 17.6 |
| 56.3 | 1.1 | 5.0 | 1.3 | 100 | 19.3 | 18.0 | 9.8 |
| 44.0 | 1.4 | 3.5 | 0.8 | 90 | 15.3 | 14.1 | 5.3 |
| | | | | 80 | 9.9 | 8.9 | 1.5 |
| | | | | 70 | 4.8 | 3.2 | 0.2 |
| | | | | 60 | 3.6 | 0.3 | 0.1 |
| | | | | 50 | 6.7 | 0.0 | 0.2 |
| | | | | 40 | 8.2 | 0.1 | 2.0 |
| Ce-139 Invention | | | | | | | |
| 194.5 | 0.3 | 2.1 | 0.2 | 200 | 1.7 | 4.9 | 1.7 |
| 178.3 | 0.7 | 2.2 | 0.2 | 190 | 1.5 | 4.9 | 1.5 |
| 160.7 | 1.0 | 2.1 | 0.1 | 180 | 1.4 | 4.7 | 1.4 |
| 141.8 | 1.3 | 1.9 | 0.2 | 170 | 1.3 | 4.5 | 1.3 |
| 120.9 | 1.6 | 1.5 | 0.1 | 160 | 1.2 | 4.9 | 1.2 |
| 97.0 | 2.0 | 1.1 | 0.2 | 150 | 1.1 | 4.6 | 1.1 |
| 90.8 | 0.4 | 0.9 | 0.4 | 140 | 0.9 | 4.7 | 1.0 |
| 81.7 | 0.6 | 0.9 | 0.6 | 130 | 0.8 | 4.5 | 0.9 |
| 72.8 | 0.7 | 0.2 | 0.0 | 120 | 0.7 | 4.6 | 0.7 |
| 64.9 | 0.9 | — | — | 110 | 0.5 | 4.6 | 0.6 |
| 56.3 | 1.1 | — | — | 100 | 0.4 | 4.6 | 1.8 |
| 44.0 | 1.4 | — | — | 90 | 0.3 | 4.3 | 1.3 |
| | | | | 80 | 0.2 | 4.0 | 0.9 |
| | | | | 70 | 0.1 | 3.9 | 0.7 |
| | | | | 60 | 0.1 | 3.4 | 0.2 |
| | | | | 50 | 0.1 | 3.2 | 0.1 |
| | | | | 40 | 0.0 | 3.0 | 0.0 |
| Ce-141 Invention | | | | | | | |
| 194.5 | 0.3 | 13.1 | 0.9 | 200 | 12.6 | 14.5 | 24.3 |
| 178.3 | 0.7 | 15.8 | 1.2 | 190 | 13.2 | 16.5 | 25.3 |
| 160.7 | 1.0 | 16.3 | 4.0 | 180 | 13.7 | 16.8 | 25.9 |
| 141.8 | 1.3 | 17.0 | 1.9 | 170 | 14.0 | 17.2 | 26.5 |
| 120.9 | 1.6 | 19.8 | 1.4 | 160 | 14.5 | 18.0 | 27.1 |
| 97.0 | 2.0 | 24.5 | 2.7 | 150 | 15.4 | 15.9 | 29.2 |
| 90.8 | 0.4 | 24.7 | 1.2 | 140 | 15.8 | 16.4 | 29.8 |
| 81.7 | 0.6 | 25.9 | 1.2 | 130 | 16.9 | 18.8 | 31.7 |
| 72.8 | 0.7 | 26.5 | 1.2 | 120 | 18.0 | 20.0 | 31.9 |
| 64.9 | 0.9 | 28.1 | 1.2 | 110 | 19.5 | 20.9 | 34.3 |

TABLE 3-continued

Cross sections measured in the invention and the predictions of MCNP6 event generators CEM03.03, Bertini, and ABLA + INCL

|  |  |  |  |  | MCNP6 Event Generators | | |
|---|---|---|---|---|---|---|---|
| Energy (MeV) | ΔE (MeV) | σ (mb) | Δσ (mb) | E (MeV) | CEM03.03 (mb) | Bertini (mb) | INCL + RAL (mb) |
| 56.3 | 1.1 | 28.4 | 1.1 | 100 | 20.4 | 21.3 | 31.8 |
| 44.0 | 1.4 | 30.4 | 1.6 | 90 | 21.0 | 22.6 | 33.6 |
|  |  |  |  | 80 | 21.6 | 23.8 | 35.5 |
|  |  |  |  | 70 | 22.6 | 24.3 | 38.6 |
|  |  |  |  | 60 | 23.1 | 23.8 | 41.7 |
|  |  |  |  | 50 | 24.9 | 25.2 | 44.8 |
|  |  |  |  | 40 | 29.7 | 26.4 | 49.7 |
| Ce-143 Invention |  |  |  |  |  |  |  |
| 194.5 | 0.3 | 7.7 | 0.5 | 200 | 9.4 | 11.2 | 17.6 |
| 178.3 | 0.7 | 9.3 | 0.7 | 190 | 10.0 | 11.3 | 18.4 |
| 160.7 | 1.0 | 9.6 | 0.6 | 180 | 10.0 | 11.4 | 18.9 |
| 141.8 | 1.3 | 10.9 | 0.7 | 170 | 10.6 | 11.6 | 19.6 |
| 120.9 | 1.6 | 13.4 | 1.6 | 160 | 10.7 | 12.2 | 19.8 |
| 97.0 | 2.0 | 15.2 | 1.7 | 150 | 11.6 | 12.4 | 21.2 |
| 90.8 | 0.4 | 15.2 | 0.8 | 140 | 12.3 | 12.9 | 21.6 |
| 81.7 | 0.6 | 16.4 | 0.8 | 130 | 12.9 | 13.3 | 22.9 |
| 72.8 | 0.7 | 17.8 | 0.8 | 120 | 13.9 | 13.6 | 23.4 |
| 64.9 | 0.9 | 19.9 | 1.0 | 110 | 15.1 | 14.4 | 24.6 |
| 56.3 | 1.1 | 21.7 | 1.0 | 100 | 16.2 | 16.7 | 21.7 |
| 44.0 | 1.4 | 24.3 | 1.4 | 90 | 17.1 | 17.3 | 23.5 |
|  |  |  |  | 80 | 17.7 | 16.4 | 26.0 |
|  |  |  |  | 70 | 18.1 | 17.4 | 28.6 |
|  |  |  |  | 60 | 18.2 | 17.1 | 31.2 |
|  |  |  |  | 50 | 19.8 | 18.9 | 36.2 |
|  |  |  |  | 40 | 23.7 | 20.0 | 38.7 |
| La-140 Invention |  |  |  |  |  |  |  |
| 194.5 | 0.3 | 2.6 | 0.2 | 200 | 4.0 | 3.6 | 6.0 |
| 178.3 | 0.7 | 2.8 | 0.4 | 190 | 3.9 | 3.8 | 6.2 |
| 160.7 | 1.0 | 3.2 | 0.3 | 180 | 4.0 | 4.0 | 6.6 |
| 141.8 | 1.3 | 3.5 | 0.3 | 170 | 4.3 | 4.1 | 6.3 |
| 120.9 | 1.6 | 3.9 | 0.2 | 160 | 4.3 | 4.2 | 6.0 |
| 97.0 | 2.0 | 4.9 | 0.7 | 150 | 4.4 | 4.3 | 6.3 |
| 90.8 | 0.4 | 4.9 | 0.3 | 140 | 4.5 | 4.2 | 6.1 |
| 81.7 | 0.6 | 5.3 | 0.3 | 130 | 4.6 | 4.4 | 6.2 |
| 72.8 | 0.7 | 5.8 | 0.3 | 120 | 4.8 | 4.4 | 6.5 |
| 64.9 | 0.9 | 6.0 | 0.3 | 110 | 4.8 | 4.4 | 6.3 |
| 56.3 | 1.1 | 5.6 | 0.4 | 100 | 5.0 | 4.6 | 8.3 |
| 44.0 | 1.4 | 3.9 | 0.6 | 90 | 5.0 | 5.0 | 9.1 |
|  |  |  |  | 80 | 4.8 | 5.2 | 10.3 |
|  |  |  |  | 70 | 4.6 | 5.0 | 10.8 |
|  |  |  |  | 60 | 4.9 | 5.5 | 10.4 |
|  |  |  |  | 50 | 5.3 | 5.3 | 8.6 |
|  |  |  |  | 40 | 6.0 | 5.2 | 5.9 |
| Ba-140 Invention |  |  |  |  |  |  |  |
| 194.5 | 0.3 | 8.0 | 0.8 | 200 | 8.6 | 13.3 | 19.7 |
| 178.3 | 0.7 | 10.0 | 0.8 | 190 | 9.0 | 13.8 | 20.7 |
| 160.7 | 1.0 | 10.6 | 0.8 | 180 | 9.4 | 14.4 | 21.1 |
| 141.8 | 1.3 | 12.0 | 0.8 | 170 | 10.0 | 14.3 | 22.3 |
| 120.9 | 1.6 | 13.6 | 0.9 | 160 | 10.4 | 14.5 | 23.4 |
| 97.0 | 2.0 | 16.8 | 1.9 | 150 | 11.2 | 15.7 | 23.8 |
| 90.8 | 0.4 | 17.1 | 1.1 | 140 | 12.0 | 15.5 | 25.3 |
| 81.7 | 0.6 | 18.5 | 1.1 | 130 | 13.0 | 17.1 | 26.6 |
| 72.8 | 0.7 | 19.7 | 1.2 | 120 | 14.2 | 17.3 | 27.6 |
| 64.9 | 0.9 | 22.3 | 1.4 | 110 | 15.5 | 17.9 | 29.7 |
| 56.3 | 1.1 | 25.8 | 1.4 | 100 | 16.9 | 19.6 | 24.1 |
| 44.0 | 1.4 | 30.9 | 2.0 | 90 | 18.0 | 20.0 | 25.7 |
|  |  |  |  | 80 | 18.8 | 21.0 | 27.1 |
|  |  |  |  | 70 | 19.9 | 21.6 | 30.0 |
|  |  |  |  | 60 | 20.6 | 22.6 | 34.3 |
|  |  |  |  | 50 | 21.7 | 23.2 | 40.1 |
|  |  |  |  | 40 | 27.1 | 24.2 | 48.1 |

Yield Calculations for Actinium, Lanthanum, and Cerium Radioisotopes

Yields for the discussed radioisotopes of actinium, lanthanum and cerium have been calculated using the measured and computationally predicted cross sections reported above. In order to facilitate comparison with other values previously reported in the literature [J. W. Weidner, S. G. Mashnik, K. D. John, F. Hemez, B. D. Ballard, H. Bach, E. R. Birnbaum, L. J. Bitteker, A. Couture, D. Dry, M. E. Fassbender, M. S. Guley, K. R. Jackman, J. L. Ullman, L. E. Wolfsberg, F. M. Nortier, Proton-induced cross sections relevant to production of $^{225}$Ac and $^{223}$Ra in natural thorium targets below 200 MeV, Applied Radiation and Isotopes, 70 (2012) 2602-2607], targets of 5 g cm-2 thickness and proton beam energies and intensities typical of irradiations at the LANL Isotope Production Facility (IPF) and the Brookhaven Linac Isotope Producer (BLIP) were assumed for these calculations. Ten-day irradiations were used and values reported coincide with the end of bombardment. In the case of La-140, yield values include contributions from decay of the Ba-140 parent during irradiation. All values are collected below in Table 4.

TABLE 4

Yield calculations for radioisotopes discussed above assuming irradiation parameters detailed in text and typical of LANL IPF and BNL BLIP facilities

| Isotope | IPF Yield (250 μA, 93-72 MeV) | | BLIP Yield (100 μA, 195-183 MeV) | |
|---|---|---|---|---|
| | (GBq) | (Ci) | (GBq) | (Ci) |
| $^{225}$Ac[a] | 52 | 1.4 | 74 | 2.0 |
| $^{226}$Ac | 66 | 1.8 | 170 | 4.6 |
| $^{227}$Ac | 0.1 | 3E-3 | 0.2 | 5E-3 |
| $^{139}$Ce | 0.7 | 0.02 | 1.6 | 4E-2 |
| $^{141}$Ce | 103 | 2.8 | 42 | 1.1 |
| $^{143}$Ce | 347 | 9.4 | 127 | 3.4 |
| $^{140}$La[b] | 43 | 1.2 | 43 | 1.2 |
| $^{140}$La[c] | 46 | 1.3 | 170 | 4.6 |
| $^{134}$Ce[d] | 4E-3 | 1E-4 | 0.4 | 1E-2 |
| $^{135}$Ce[d] | 4E-3 | 1E-4 | 1.1 | 3E-2 |
| $^{144}$Ce[d] | 7.5 | 0.2 | 3.1 | 0.08 |
| $^{135}$La[d] | 1.1 | 0.03 | 14 | 0.4 |
| $^{137}$La[d] | 5E-6 | 1E-7 | 1.3E-5 | 4E-7 |

Figure 1B:
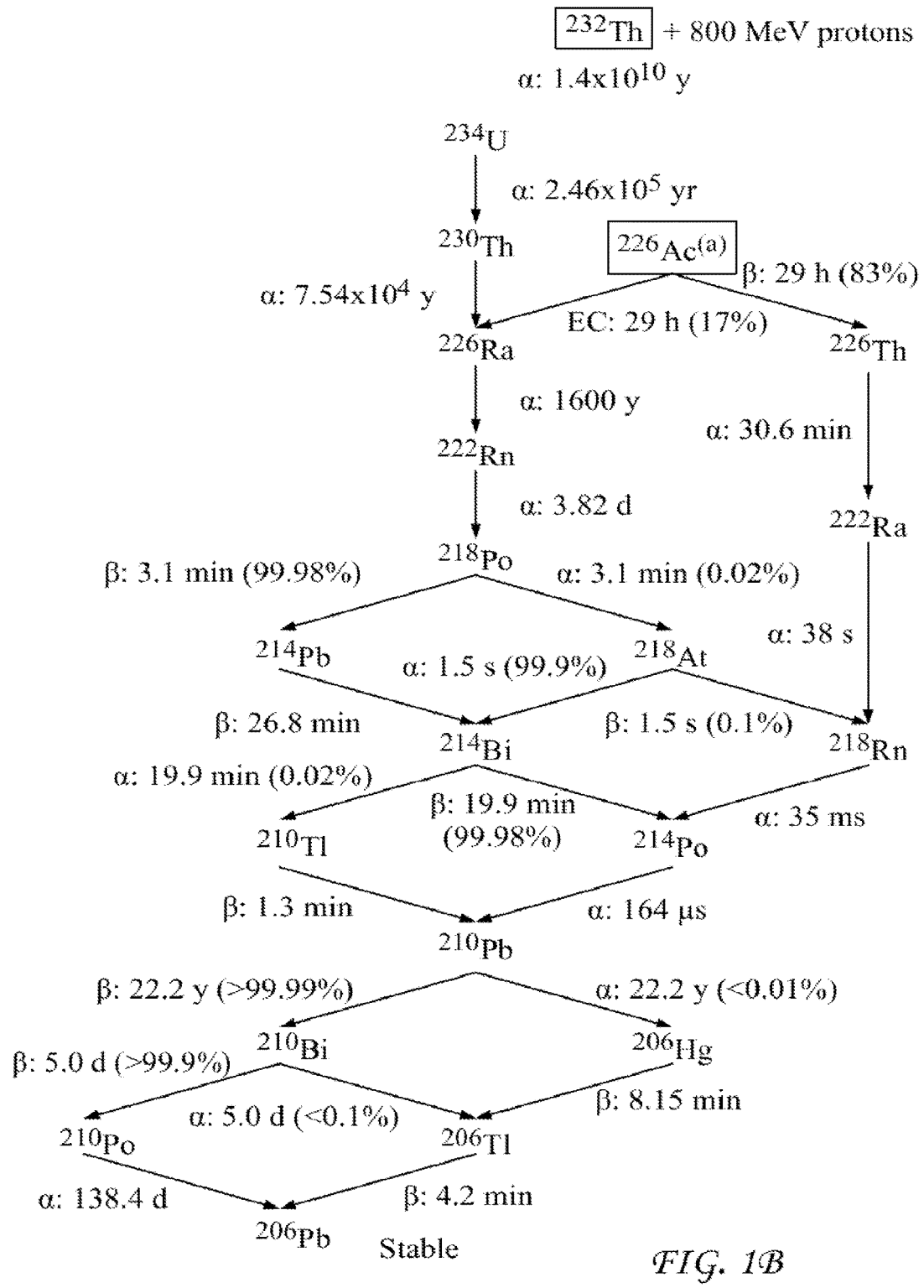
Figure 1C:
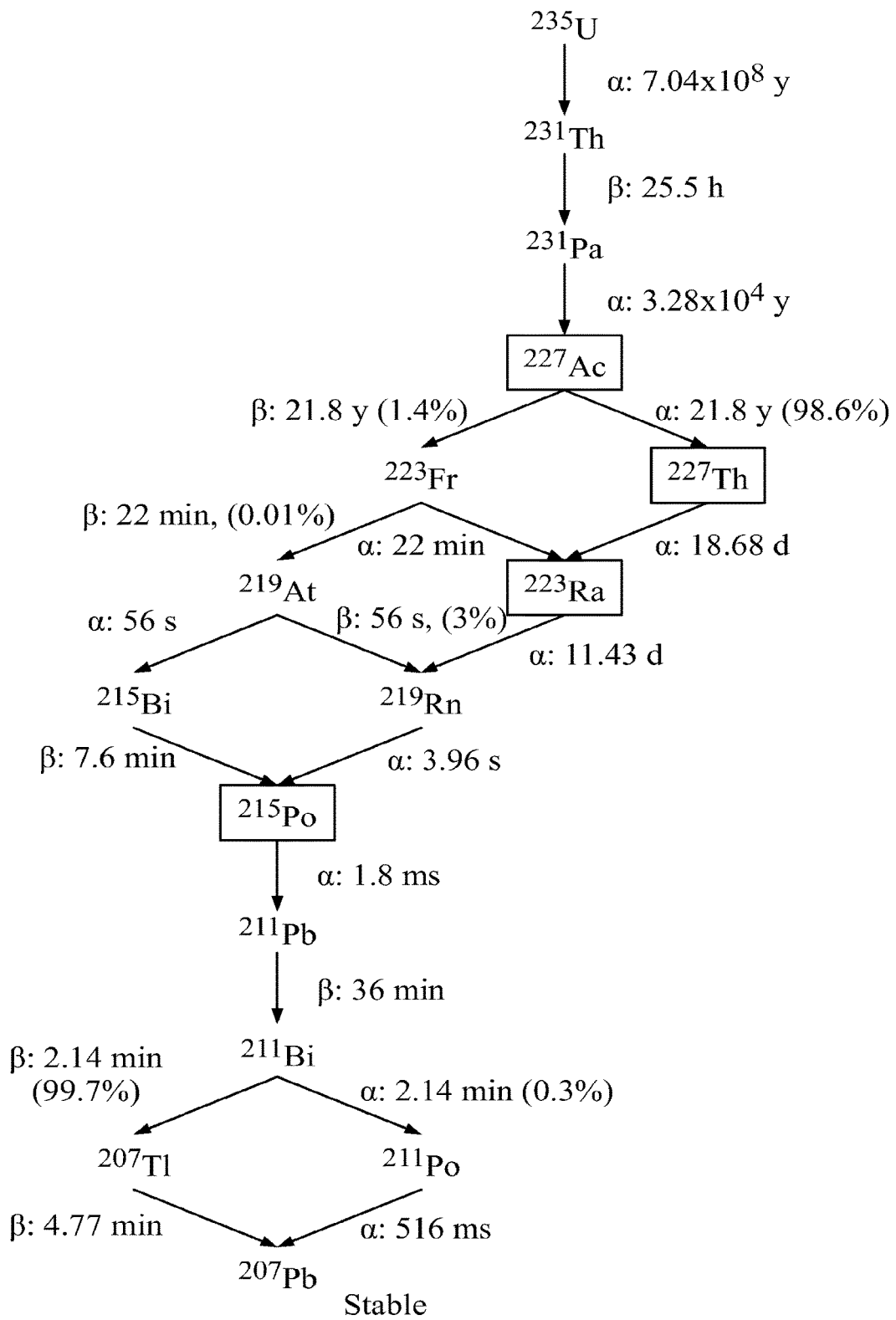
Figure 6:
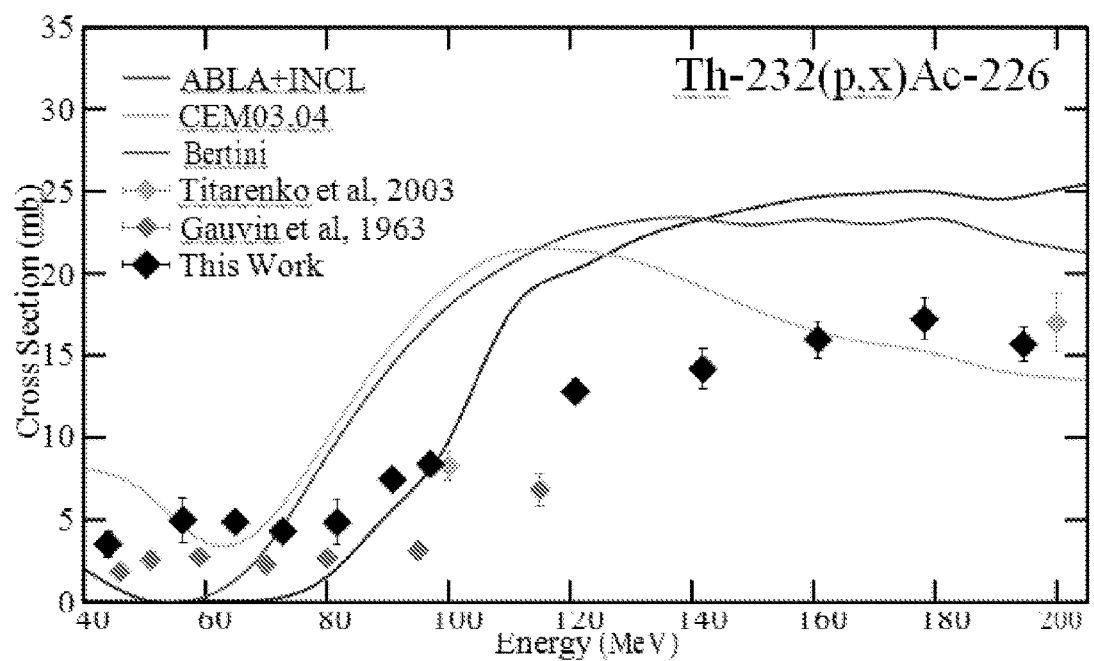
FIG. 6 depicts a comparison of calculated Ac-226 cross sections with experimentally measured data from an embodiment of the present invention and from others.
Figure 7:
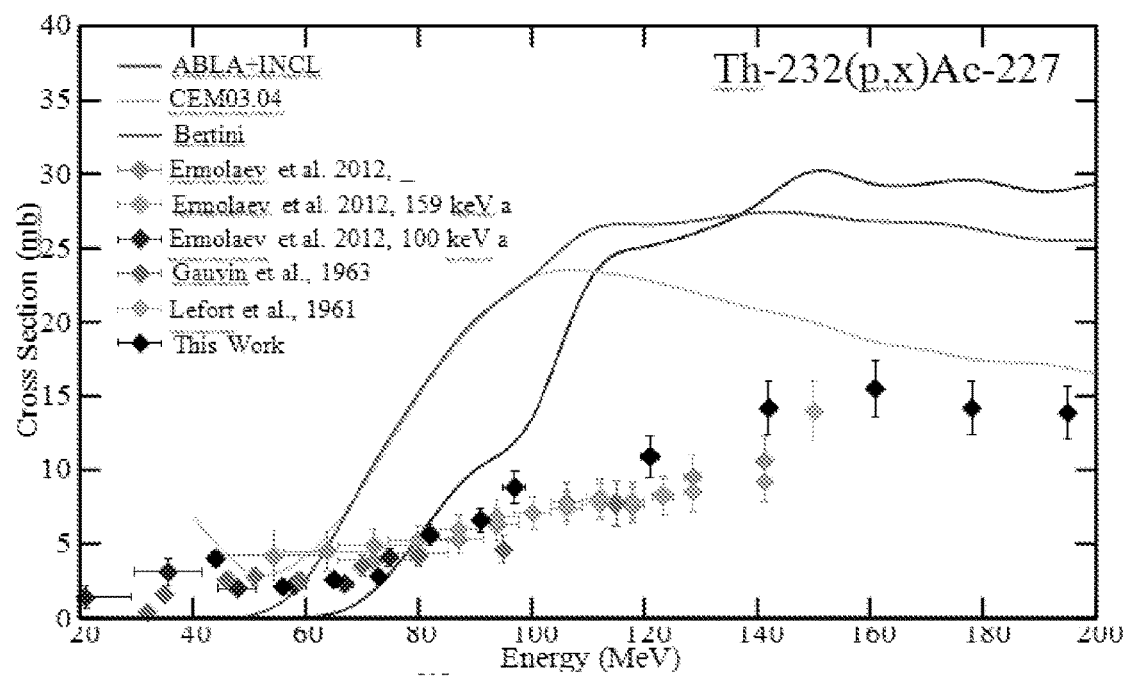
FIG. 7 depicts a comparison of calculated Ac-227 cross sections with experimentally measured data from the present and the present invention and from others.
Figure 8:
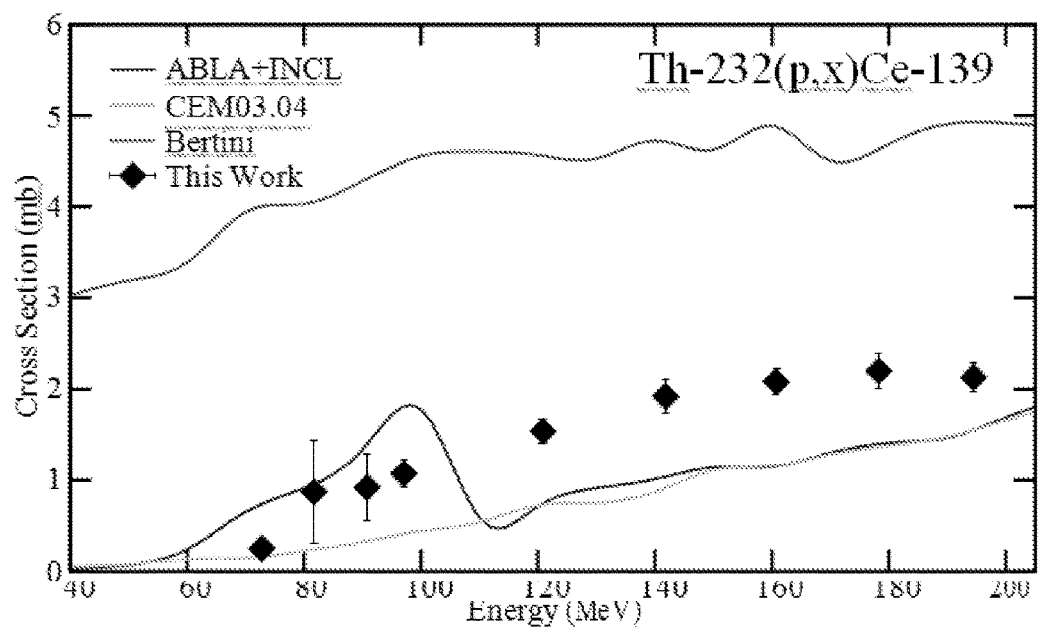
FIG. 8 depicts a comparison of calculated Ce-139 cross sections with experimentally measured data from an embodiment of the present invention.
Figure 9:
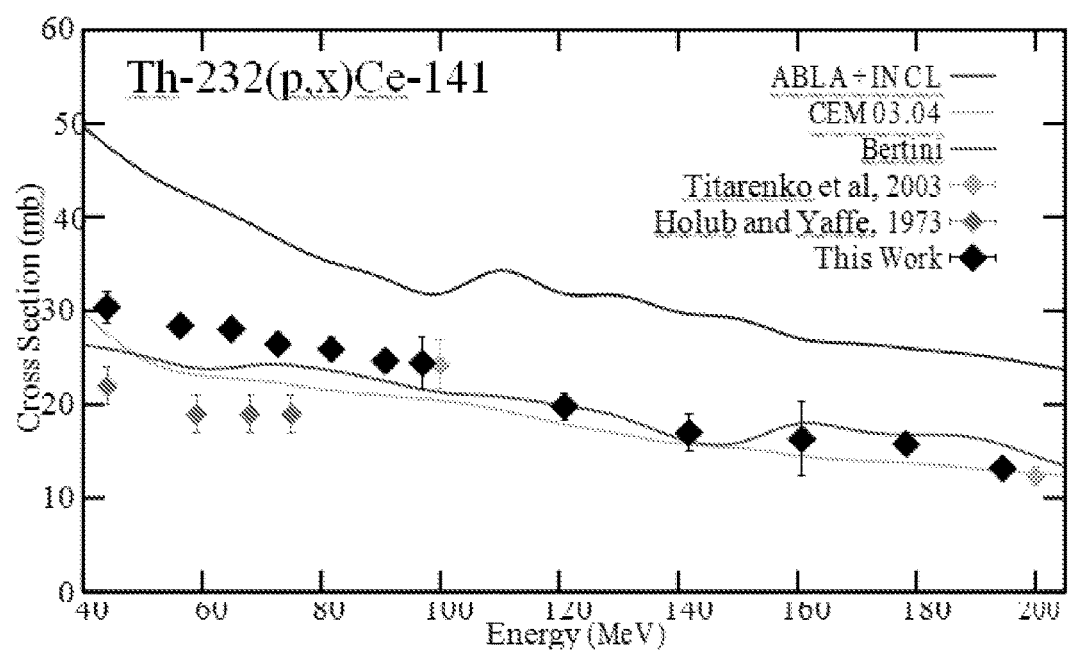
FIG. 9 depicts a comparison of calculated Ce-141 cross sections with experimentally measured data from the present invention and from others.
Figure 10:
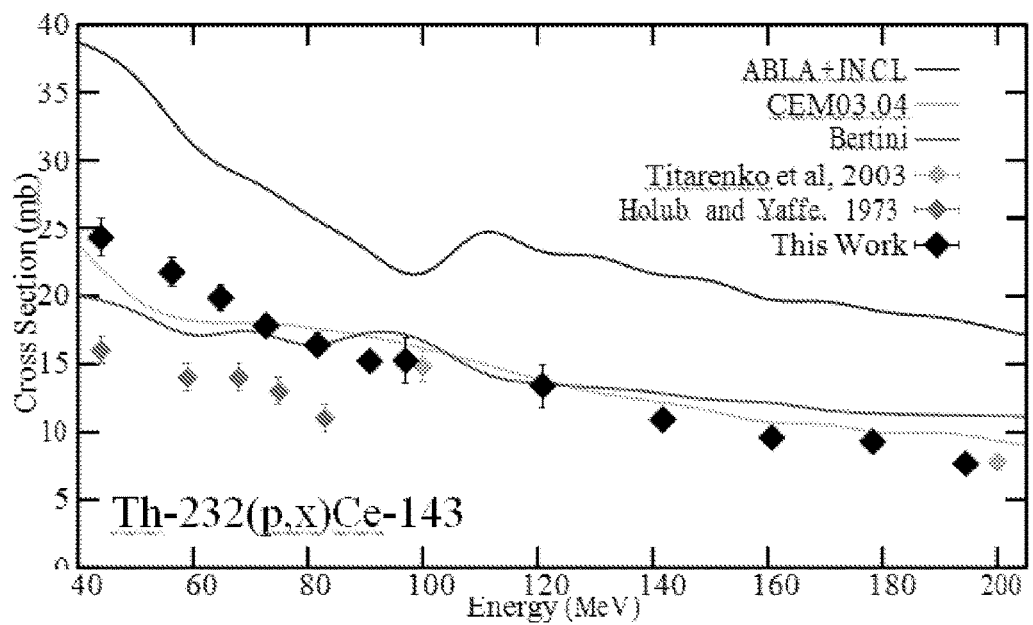
FIG. 10 depicts a comparison of calculated Ce-143 cross sections with experimentally measured data from the present invention and from others.
Figure 11:
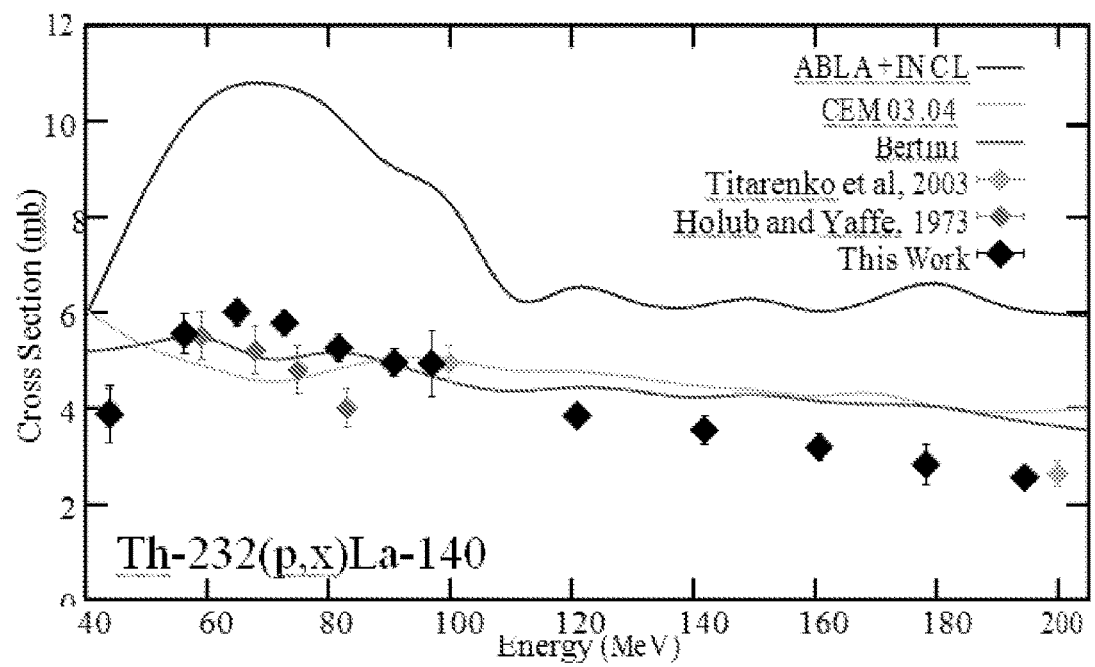
FIG. 11 depicts a comparison of calculated, independent La-140 cross sections with experimentally measured data from the present invention and from others.
Figure 12:
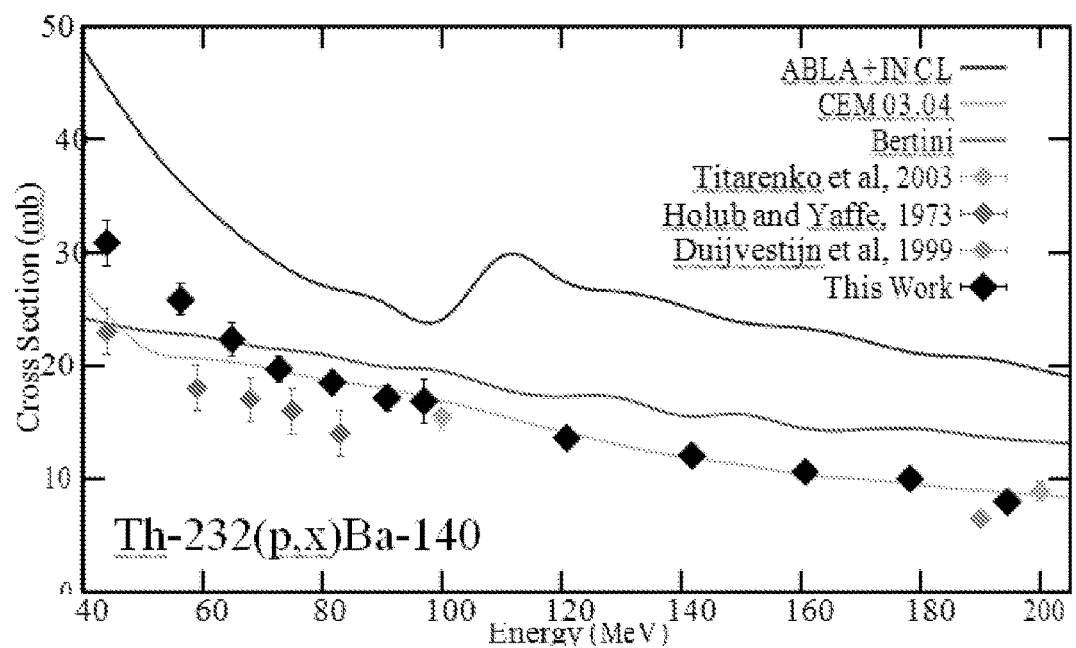
FIG. 12 depicts a comparison of calculated Ba-140 cross sections with experimentally measured data from the present invention and from others.
Figure 13:
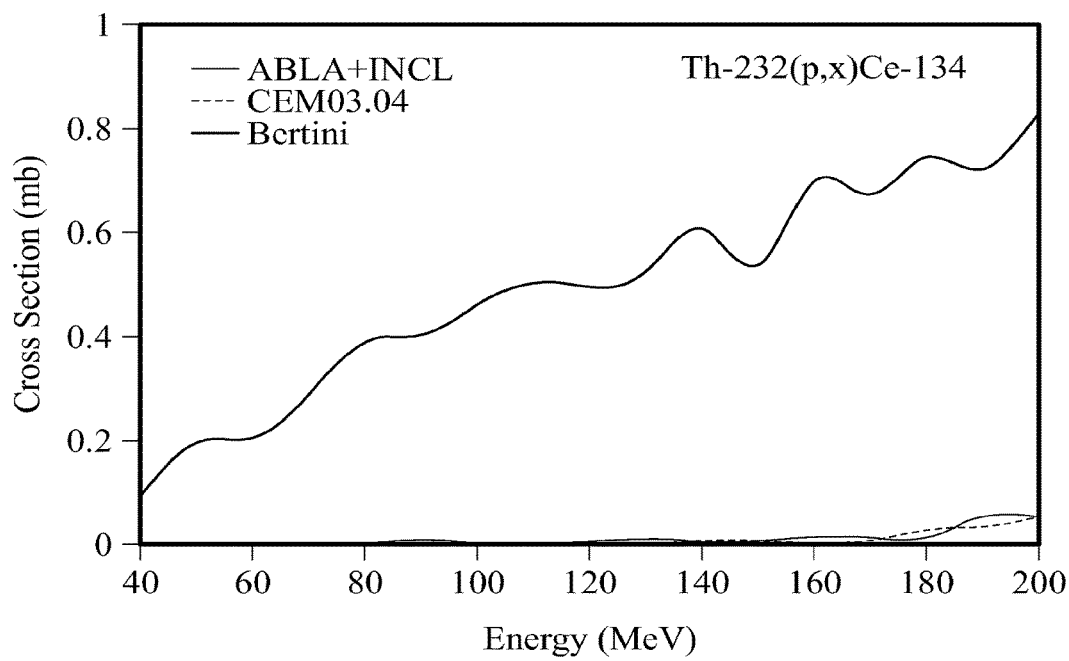
FIGS. 13-17 depict plots of MCNP6 event generator predictions for Ce-134, Ce-135, Ce-144, La-135, and La-137 respectively compared with measured data from an embodiment of the present invention, where available.
Figure 14:
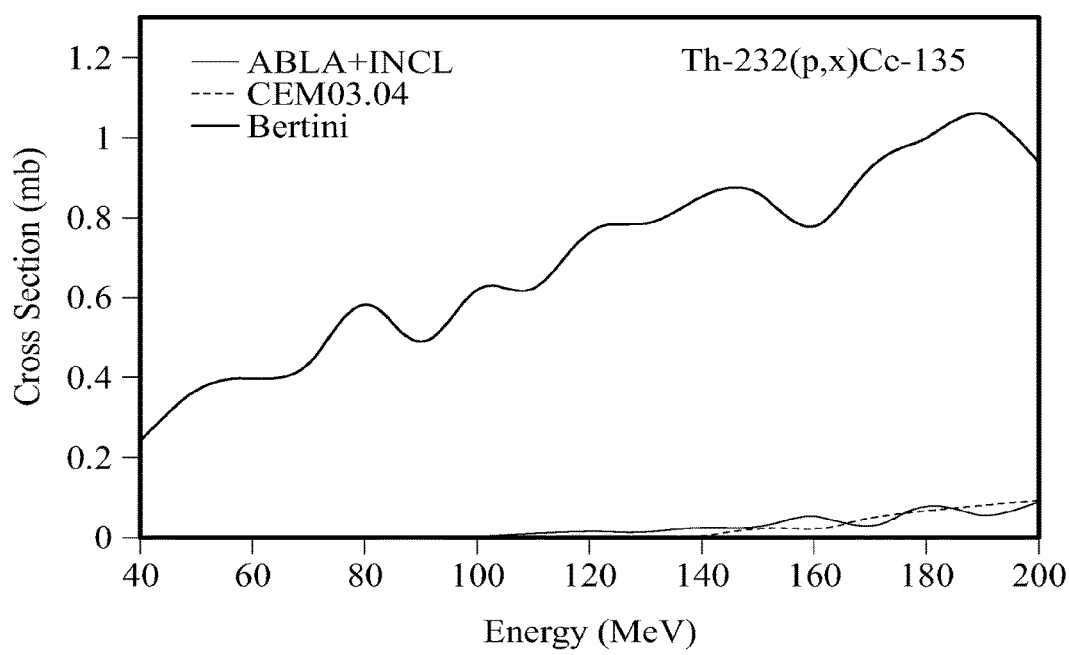
Figure 15:
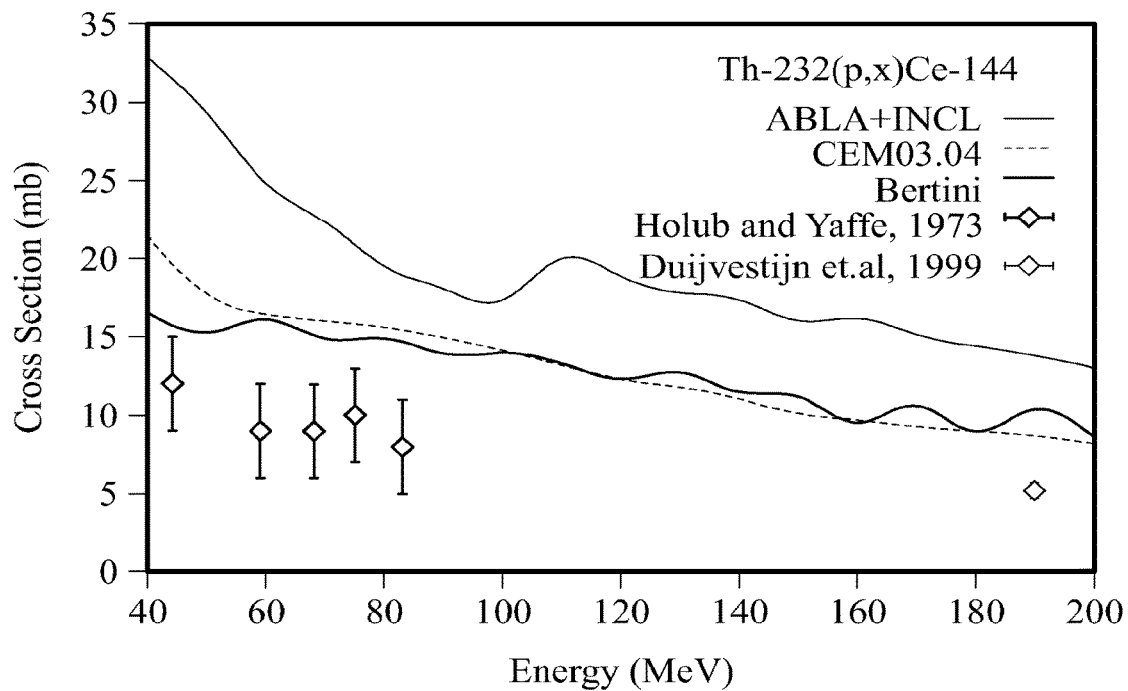
Figure 16:
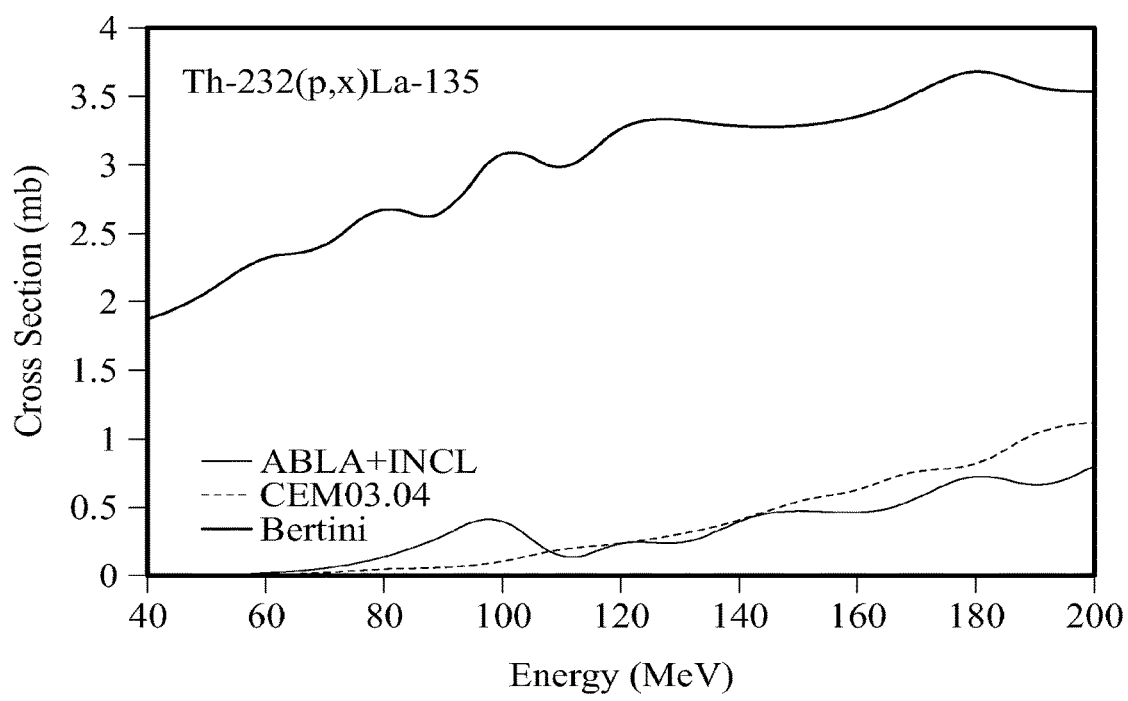
Figure 17:
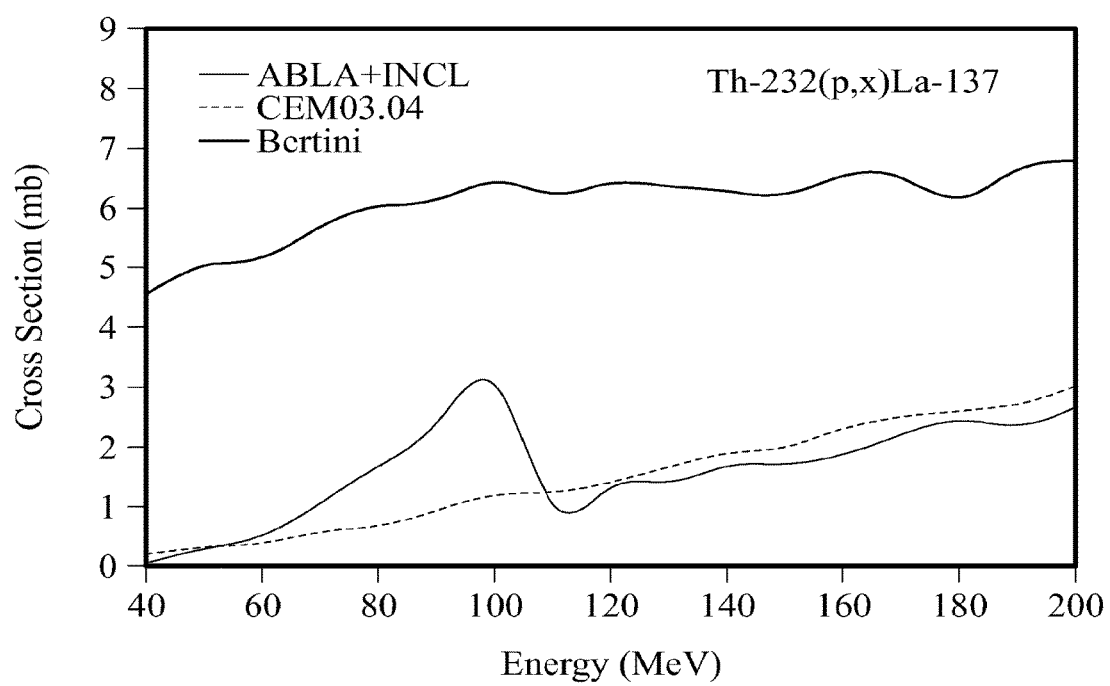

[a]S. V. Ermolaev, B. L. Zhuikov, V. M. Kokhanyuk, V. L. Matushko, S. N. Kalmykov, R. A. Aliev, I. G. Taranaev, B. F. Myasoedov, Production of actinium, thorium and radium isotopes from natural thorium targets irradiated with protons up to 141 MeV, Radiochimica Acta, 100 (2012) 223-229
[b]yields calculated from the direct reaction
[c]yields calculated from indirect formation via decay of $^{140}$Ba parent as discussed in text
[d]yields calculated using cross section predictions of the CEM03.03 event generator These predicted yields suggest irradiation parameters tailored to the capabilities of separations chemistry development and especially to its timing. If, for example, in the preparation of Ac-225/Bi-213 generators, the Bi-210 daughter (t½=5.0 d, 99.9% β) of Ac-226 creates dosimetric conditions that are unacceptable for the patient (see FIGS. 1A-1C), generators will require an initial flush to wash accumulated Bi-210 from the column. Such a problem would be minimized by lower energy irradiation, as the cross section for Ac-226 production rises by approximately three-fold between 70 and 200 MeV (FIG. 6). Alternatively, production of cerium radiolanthanides would be minimized by irradiations at higher proton energies. Based on the predictions of the CEM03.03 event generator, chosen for its superior agreement with measured data reported here, no isotopes of lanthanum or cerium whose cross sections were not experimentally described above are expected to decrease final Ac-225 radioisotopic purity.

Measured cross sections reported in Engle, et al. for actinium, cerium, and lanthanum radioisotopes span the energy range below 200 MeV. For Ac-226, Ac-227, Ce-141, Ce-143, La-140 and its parent Ba-140, these new data extend previous measurements' energy ranges to fully cover production proton beam energies available at the Institute for Nuclear Research in Moscow, at Brookhaven National Laboratory on Long Island, and at Los Alamos National Laboratory in New Mexico. These data are the first reported measurements between 40 and 200 MeV for Ce-139. All data are expected to be relevant to irradiation and chemical separation plans used to produce Ac-225 from thorium targets for medical use.

What is claimed:

1. A method of treating cancer in a patient comprising administering to the patient an actinium-225 composition comprising the following quotient of activity quantity ratios:

actinium-226/actinium-225 less than 1;

actinium-227/actinium-225 less than 0.03;

cerium-139/actinium-225 less than 0.3;

cerium-141/actinium-225 less than 30;

cerium-143/actinium-225 less than 1; and lanthanum-140/actinium-225 less than 1.

2. The method of claim 1, wherein the cancer is breast cancer, a leukemia, a lymphoma, brain cancer, or bone cancer.

* * * * *